US00PP24814P2

(12) United States Plant Patent
Lerner

(10) Patent No.: US PP24,814 P2
(45) Date of Patent: Aug. 26, 2014

(54) *LANTANA* PLANT NAMED 'ARIES LION'

(50) Latin Name: *Lantana camara*
Varietal Denomination: Aries Lion

(71) Applicant: Arie Lerner, Kfar Aviv (IL)

(72) Inventor: Arie Lerner, Kfar Aviv (IL)

(73) Assignee: Amerinova Properties LLC, Bonsall, CA (US)

( * ) Notice: Subject to any disclaimer, the term of this patent is extended or adjusted under 35 U.S.C. 154(b) by 7 days.

(21) Appl. No.: 13/694,823

(22) Filed: Jan. 7, 2013

(51) Int. Cl.
*A01H 5/00* (2006.01)

(52) U.S. Cl.
USPC ..... Plt./227

(58) Field of Classification Search
USPC ..... Plt./227
See application file for complete search history.

*Primary Examiner* — Anne Grunberg
(74) *Attorney, Agent, or Firm* — C. A. Whealy

(57) ABSTRACT

A new and distinct cultivar of *Lantana* plant named 'Aries Lion', characterized by its compact, upright to outwardly spreading and mounding plant habit; freely branching growth habit; variegated leaves; freely flowering habit; flowers that are initially yellow in color and with development become bright orange and burnt orange to eventually red in color; and good garden performance.

1 Drawing Sheet

Botanical designation: *Lantana camara.*
Cultivar denomination: 'ARIES LION'.

BACKGROUND OF THE INVENTION

The present invention relates to a new and distinct cultivar of *Lantana* plant, botanically known as *Lantana camara* and hereinafter referred to by the name 'Aries Lion'.

The new *Lantana* plant is a naturally-occurring whole plant mutation of an unnamed selection of *Lantana camara*, not patented. The new *Lantana* plant was discovered and selected by the Inventor as a single flowering plant from within a population of plants of the parent selection in a controlled greenhouse environment in Kfar Aviv, Israel in 2008.

Asexual reproduction of the new *Lantana* plant by vegetative cuttings in a controlled greenhouse environment in Kfar Aviv, Israel since 2008 has shown that the unique features of this new *Lantana* plant are stable and reproduced true to type in successive generations.

SUMMARY OF THE INVENTION

Plants of the new *Lantana* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Aries Lion'. These characteristics in combination distinguish 'Aries Lion' as a new and distinct *Lantana* plant:

1. Compact, upright to outwardly spreading and mounding plant habit.
2. Freely branching growth habit.
3. Variegated leaves.
4. Freely flowering habit.
5. Flowers that are initially yellow in color and with development become bright orange and burnt orange to eventually red in color.
6. Good garden performance.

Plants of the new *Lantana* can be compared to plants of the parent selection. Plants of the new *Lantana* differ from plants of the parent selection in the following characteristics:

1. Plants of the new *Lantana* have variegated leaves whereas plants of the parent selection have solid green-colored leaves'.
2. Plants of the new *Lantana* and the parent selection differ in flower color as plants of the parent selection have red-colored flowers.

Plants of the new *Lantana* can be compared to plants of the *Lantana camara* 'Bante Rossa', disclosed in U.S. Plant Pat. No. 18,148. Plants of the new *Lantana* differ from plants of 'Bante Rossa' in the following characteristics:

1. Plants of the new *Lantana* are more vigorous than and not as compact as plants of 'Bante Rossa'.
2. Plants of the new *Lantana* and 'Bante Rossa' differ in leaf color as plants of 'Bante Rossa' have solid green-colored leaves.
3. Plants of the new *Lantana* and 'Bante Rossa' differ in flower color as plants of 'Bante Rossa' have purple pink and yellow-colored flowers.

BRIEF DESCRIPTION OF THE PHOTOGRAPHS

The accompanying colored photographs illustrate the overall appearance of the new *Lantana* plant showing the colors as true as it is reasonably possible to obtain in colored reproductions of this type. Colors in the photographs may differ slightly from the color values cited in the detailed botanical description which accurately describe the colors of the new *Lantana* plant.

The photograph at the bottom of the sheet comprises a side perspective view of a typical flowering plant of 'Aries Lion' grown in a container.

The photograph at the top of the sheet is a close-up view of a typical flowering plant of 'Aries Lion'.

DETAILED BOTANICAL DESCRIPTION

The aforementioned photographs and following observations and measurements describe plants grown during the early autumn in one-gallon containers in an outdoor nursery in Bonsall, Calif. and under commercial practices typical of commercial production. During the production of the plants, day temperatures ranged from 21° C. to 35° C. and night temperatures ranged from 13° C. to 18° C. Plants were pinched one time at planting and were twelve weeks old when the photographs and the description were taken. In the following description, color references are made to The Royal Horticultural Society Colour Chart, 2007 Edition, except where general terms of ordinary dictionary significance are used.

Botanical classification: *Lantana camara* 'Aries Lion'.

Parentage: Naturally-occurring whole plant mutation of an unnamed selection of *Lantana camara*, not patented.

Propagation:

*Type*.—By vegetative cuttings.

*Time to initiate roots, summer*.—About ten days at temperatures of 16° C.

*Time to initiate roots, winter*.—About 14 days at temperatures of 16° C.

*Time to produce a rooted young plant, summer*.—About 18 days at temperatures of 16° C.

*Time to produce a rooted young plant, winter*.—About 21 days at temperatures of 16° C.

*Root description*.—Fleshy; thin; white in color.

*Rooting habit*.—Moderately freely branching; medium density.

Plant description:

*Plant and growth habit*.—Compact, upright and outwardly spreading and mounding plant habit; vigorous growth habit and moderate growth rate.

*Plant height*.—About 36 cm.

*Plant diameter*.—About 68 cm.

Lateral branch description:

*Branching habit*.—Freely branching habit with about five primary lateral branches per plant; each primary lateral branch with potentially two secondary lateral branches developing at every node; pinching enhances lateral branch development.

*Length*.—About 37 cm.

*Diameter*.—About 3 mm to 7 mm.

*Internode length*.—About 3.8 cm.

*Strength*.—Strong.

*Texture*.—Pubescent; coarse; longitudinally ridged.

*Color, young stems*.—Close to 146C.

*Color, mature stems*.—Close to 199B to 199C.

Foliage description:

*Arrangement*.—Opposite, simple.

*Length*.—About 6.4 cm.

*Width*.—About 3.6 cm.

*Shape*.—Elliptic.

*Apex*.—Acute.

*Base*.—Attenuate.

*Margin*.—Serrate.

*Texture, upper and lower surfaces*.—Pubescent, coarse and rough; somewhat leathery.

*Venation pattern*.—Pinnate; arcuate to reticulate.

*Color*.—Developing leaves, upper surface: Close to 146B to 146C. Developing leaves, lower surface: Close to 147C. Fully expanded leaves, upper surface: Center, close to 147B; interveinal areas, towards the margins and at the margins, irregular and random sectors and patches, close to 194A and NN155B to NN155B; venation, close to 147B. Fully expanded leaves, lower surface: Close to 147B to 147C; venation, close to 148C.

*Petiole length*.—About 2 cm.

*Petiole diameter*.—About 2 mm.

*Petiole texture, upper and lower surfaces*.—Pubescent.

*Petiole color, upper and lower surfaces*.—Close to 146C.

Flower description:

*Flower arrangement and flowering habit*.—Solitary tubular to somewhat salverform flowers arranged in terminal and axillary hemispherical umbels; flowers face mostly upward or outward; freely flowering habit with about 15 flowers developing per inflorescence; flowers sessile with the umbel.

*Natural flowering season*.—Plants of the new *Lantana* flower continuously from spring until frost in the autumn in Southern California; plants begin flowering about six to eight weeks after planting.

*Flower longevity on the plant*.—About two to three days; flowers not persistent.

*Fragrance*.—Fairly pungent; fruity and spicy.

*Inflorescence height*.—About 1.2 cm.

*Inflorescence diameter*.—About 2.7 cm.

*Flowers*.—Appearance: Flared trumpet, corolla fused, four-parted. Diameter: About 7 mm by 9 mm. Depth (height): About 1.2 cm. Throat diameter: About 1 mm. Tube diameter: About 1 mm. Tube length: About 8 mm.

*Flower buds*.—Length: About 8 mm. Diameter: About 2.5 mm. Shape: Elongated oblong with rounded apex. Color: Close to 175B to 175C.

*Corolla*.—Arrangement: Single whorl of four fused petals. Petal lobe length: About 4 mm to 5 mm. Petal lobe width: About 3 mm to 5 mm. Petal lobe shape: Rounded. Petal lobe apex: Rounded. Petal margin: Entire to slightly erose; curling upward. Petal texture, upper and lower surfaces: Smooth, glabrous; velvety. Throat and tube texture: Pubescent. Color: When opening, upper surface: Center, close to 15A; towards the margins, close to N163C. When opening, lower surface: Close to 20A. Fully opened, upper surface: Close to 163C; with development, color shifts to N163C to N163B to more burnt orange than 169A and eventually becoming closer to 46B. Fully opened, lower surface: Close to 179B to 179C. Throat: Close to 15B to 15C becoming closer to 31B with development. Tube: Close to 168C becoming closer to 179C with development.

*Calyx*.—Appearance: Short and narrow tubular calyx with four fused sepals. Length: About 2 mm. Diameter: About 1 mm. Sepal apex: Acute. Sepal margin: Entire. Sepal texture, inner surface: Smooth, glabrous. Sepal texture, outer surface: Pubescent. Sepal color, inner surface: Close to 145D. Sepal color, outer surface: Close to 145C.

*Peduncles*.—Length: About 4.4 cm. Diameter: About 1 mm. Strength: Strong. Texture: Pubescent. Color: Close to 146C.

*Reproductive organs*.—Stamens: Quantity and arrangement: Four per flower, adnate to floral tube. Filament length: About 4 mm. Filament color: Close to 1D. Anther length: Less than 1 mm. Anther shape: Oval.

Anther color: Close to 162A. Pollen amount: None observed. Pistils: Quantity: One per flower. Pistil length: About 3 mm. Stigma shape: Oval to nearly round. Stigma color: Close to 145B. Style length: About 1.5 mm. Style color: Close to 145D. Ovary color: Close to 145C. Fruits and seeds: Fruit and seed development have not been observed on plants of the new *Lantana*.

Garden performance: Plants of the new *Lantana* have been observed to have good garden performance and to tolerate wind, rain and temperatures ranging from about 1° C. to about 35° C.

Pathogen & pest resistance: Plants of the new *Lantana* have not been observed to be resistant to pests and pathogens common to *Lantana* plants.

It is claimed:

1. A new and distinct *Lantana* plant named 'Aries Lion' as illustrated and described.

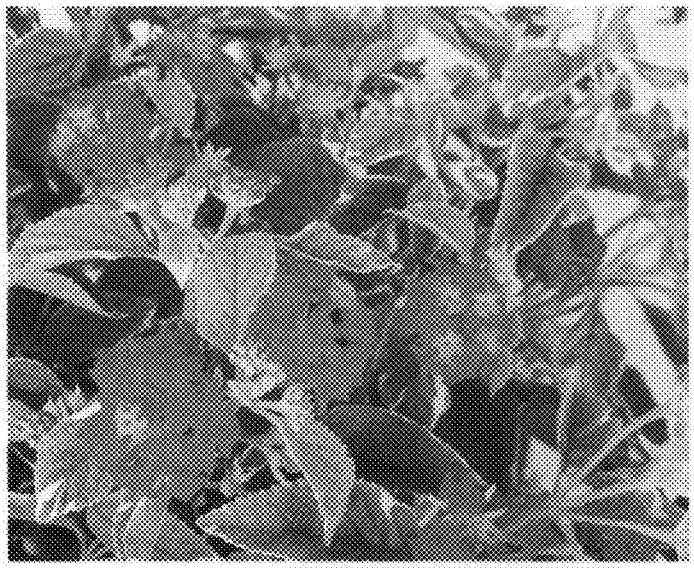
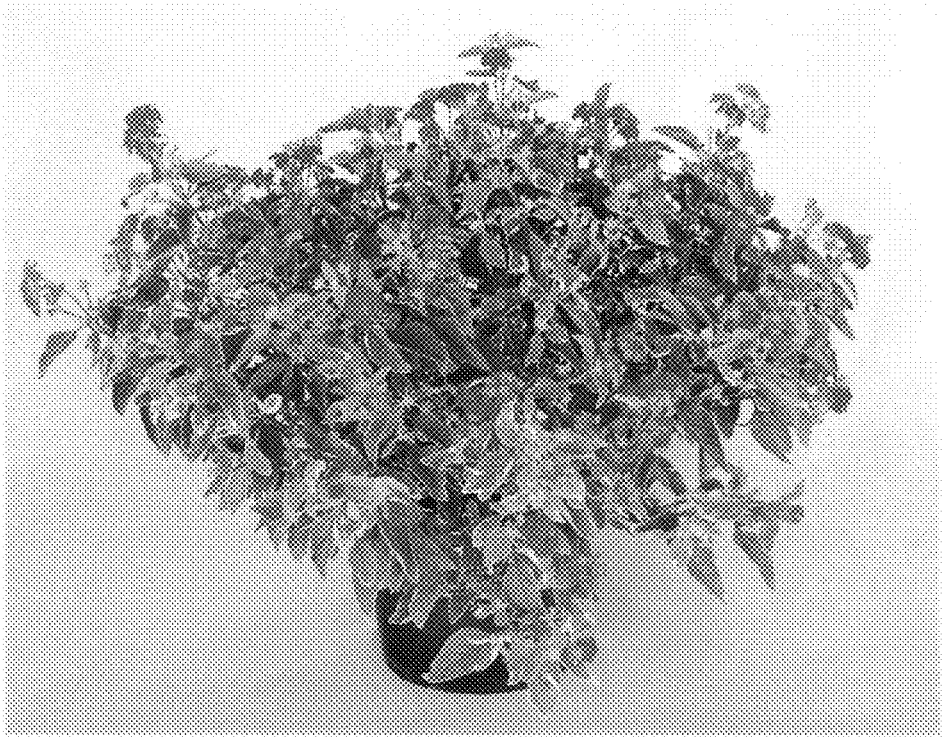

* * * * *